United States Patent [19]

Kondo et al.

[11] 4,092,482

[45] May 30, 1978

[54] PROCESS FOR PREPARING 6,6,6-TRIHALO-3,3-DIMETHYL-4-HEXENOATES

[75] Inventors: Kiyoshi Kondo; Kiyohide Matsui; Akira Negishi, all of Kanagawa; Yuriko Takahatake, Tokyo, all of Japan

[73] Assignee: Sagami Chemical Research Center, Tokyo, Japan

[21] Appl. No.: 753,077

[22] Filed: Dec. 21, 1976

[30] Foreign Application Priority Data

Dec. 26, 1975 Japan .............................. 50-154755

[51] Int. Cl.$^2$ ............................................. C07C 69/65
[52] U.S. Cl. .................................................... 560/213

[58] Field of Search ................... 260/486 D; 560/213

[56] References Cited

FOREIGN PATENT DOCUMENTS 833,278   10/1976   Belgium .......................... 210/486 D

*Primary Examiner*—Paul J. Killos
*Attorney, Agent, or Firm*—Richard L. Hansen; Henry R. Ertelt

[57] ABSTRACT

An improved process for preparing a 6,6,6-trihalo-3,3-dimethyl-4-hexenoate, intermediate in the production of pyrethroid insecticides, comprises dehydrohalogenating with an organic amine a 4,6,6,6-tetrahalo-3,3-dimethylhexanoate having a 4-halogen atom of higher atomic number than any of the 6-halogen atoms.

10 Claims, No Drawings

PROCESS FOR PREPARING 6,6,6-TRIHALO-3,3-DIMETHYL-4-HEXENOATES

Belgian Pat. No. 833,278 describes a process for making dihalovinylcyclopropanecarboxylates, which are or may be converted into pyrethroid insecticides; for example, 3-phenoxybenzyl 2-(2,2-dichlorovinyl)-3,3-dimethylcyclopropanecarboxylate. One of the intermediates in the aforesaid process is a 6,6,6-trihalo-3,3-dimethyl-4-hexenoate. As part of the aforesaid process, it is disclosed that 6,6,6-trihalo-3,3-dimethyl-4-hexenoates can be prepared by dehydrohalogenating 4,6,6,6-tetrahalo-3,3-dimethylhexanoates. According to the disclosure, successful preparation of these hexenoates requires careful control of the temperature at which the dehydrohalogenation is carried out, temperatures above 25° C leading to the formation of isomeric by-products, which are troublesome to separate. In practicing the process commercially it is difficult to maintain the temperature below 25° C, since the reaction is exothermic; to do so requires costly external cooling and the slow addition of one reactant to the other, prolonging the reaction time. In addition, the disclosed dehydrohalogenation requires the use of an aprotic solvent; diethyl ether, tetrahydrofuran, dimethylformamide and dimethylsulfoxide are specifically disclosed. These solvents are undesirable to employ on a commercial scale. The ethereal solvents present explosion hazards due to the formation of peroxides; the other solvents are either very toxic, have high boiling points making them difficult to separate from the product, or are very costly. Therefore, a commercially feasible process for dehydrohalogenating a 4,6,6,6-tetrahalo-3,3-dimethylhexanoate to produce the 6,6,6-trihalo-3,3-dimethyl-4-hexenoate intermediate would be highly desirable.

Accordingly, it is the object of this invention to provide an improved process for making a 6,6,6-trihalo-3,3-dimethyl-4-hexenoate, comparatively free of by-products, by dehydrohalogenating a 4,6,6,6-tetrahalo-3,3-dimethylhexanoate under commercially suitable conditions and to provide novel compositions of matter, products of the process, which may be converted into pyrethroid insecticides as disclosed in the prior art.

It has now been discovered that both the temperature limitation and the specific solvent requirements of the previously disclosed dehydrohalogenation can be avoided, so that the object of this invention is attained.

Thus, in a process for preparing a 6,6,6-trihalo-3,3-dimethyl-4-hexenoate by dehydrohalogenating a 4,6,6,6-tetrahalo-3,3-dimethylhexanoate, our invention is the improvement which comprises dehydrohalogenating with an organic amine a 4,6,6,6-tetrahalo-3,3-dimethylhexanoate having a 4-halogen atom of higher atomic number than any of the 6-halogen atoms, producing the 6,6,6-trihalo-3,3-dimethyl-4-hexenoate.

Although other organic amines might be employed in the dehydrohalogenation, piperidine is especially effective. Usually, between one and three moles of amine per mole of hexanoate is used.

Although a number of 4,6,6,6-tetrahalo-3,3-dimethylhexanoates may be employed, the halogen atoms in the 4-position must have a higher atomic number than any of the halogen atoms in the 6-position, and none of the halogen atoms may be iodine. Thus, chlorine or bromine may appear in the 4-position. If a bromine atom is in the 4-position, fluorine or chlorine may appear in the 6-position. If the 4-position holds a chlorine atom, the 6-position must carry fluorine. Preferably, the 4-position holds a bromine atom and the 6-position carries chlorine.

The alcohol moiety in the 4,6,6,6-tetrahalo-3,3-dimethylhexanoate should be selected from those that either appear in pyrethroid insecticides, as described in Belgian Pat. No. 833,278, such as, for example, the 3-phenoxybenzyl, α-cyano-3-phenoxybenzyl, or 5-benzyl-3-furylmethyl alcohol moieties, or are converted readily into such alcohol moieties, for example, a lower alkyl ($C_1$–$C_6$) alcohol moiety.

The process of this invention will be clarified by reference to the following specific embodiments. In the Examples which follow, temperatures are in degrees centigrade. For each boiling point (bp) taken at reduced pressure, the pressure is given in millimeters of mercury, for example, bp 116°/0.18 mm means a boiling point of 116° C at 0.18 mm of mercury. For the nmr spectra tetramethylsilane was employed as an internal standard, and in the nmr data the abbreviations have the following significance: s, singlet; d, doublet; t, triplet; q, quartet; m, multiplet. Any of these abbreviations may be preceded by b for broad or d for double, for example, d.d., double doublet; b.t., broad triplet.

EXAMPLE I

Preparation of Ethyl 3,3-Dimethyl-6,6,6-trichloro-4-hexanoate 7.08 g of ethyl 4-bromo-6,6,6-trichloro-3,3-dimethylhexanoate and 3.40 g of piperidine, the latter having been dried over potassium hydroxide, were dissolved in 18 ml of anhydrous benzene. The temperature of the reaction mixture was allowed to rise due to the exotherm, and then the reaction mixture was stirred for a total of 17.5 hours under reflux.

After the reaction mixture cooled to room temperature, it was dissolved in diethyl ether. The ethereal solution was washed with aqueous 1N hydrochloric acid to remove any excess piperidine; then the solution was washed successively with water and aqueous sodium chloride before being dried over anhydrous sodium sulfate.

The solvent was removed from the solution by distillation, and the resulting residue was distilled under reduced pressure to give 4.17 g (76% yield) of ethyl 3,3-dimethyl-6,6,6-trichloro-4-hexenoate; bp 79–84°/0.2 mm.

NMR spectrum (δ ppm, in $CCl_4$): 6.37 (d, 1H), 5.97 (d, 1H), 4.07 (q, 2H), 2.29 (s, 2H), 1.50–1.00 (m, 9H).

EXAMPLE II

Preparation of Methyl 3,3-Dimethyl-6,6,6-trichloro-4-hexenoate

To a solution of 10.2 g methyl 4-bromo-6,6,6-trichloro-3,3-dimethylhexanoate in 45 ml benzene at room temperature was added 5.11 g piperidine. The reaction mixture was heated under reflux for 20 hours.

The reaction mixture was then diluted with ether and washed successively with water, aqueous hydrochloric acid, aqueous sodium bicarbonate, and water. After it had been dried over magnesium sulfate, the ether was distilled from the reaction mixture, and the residue was distilled under reduced pressure to afford 4.79 g of methyl 3,3-dimethyl-6,6,6-trichloro-4-hexenoate; bp 68°–70°/0.11–0.12 mm.

NMR spectrum (δ ppm): 6.25 (d, 1H), 6.00 (d, 1H), 3.60 (s, 3H), 2.30 (s, 2H), 1.22 (s, 6H).

IR spectrum (peaks, cm$^{-1}$): 1740, 1650, 1440, 1240, 1125, 1080, 960, 850, 720.

Elemental analysis: Calc. for $C_9H_{13}O_2Cl_3$: C, 41.7; H, 5.1; Cl, 41.0. Found: C, 41.7; H, 5.0; Cl, 41.0.

EXAMPLE III

Preparation of 3-Phenoxybenzyl 3,3-Dimethyl-6,6,6-trichloro-4-hexenoate

In the manner of Example II, 22.1 g of 3-phenoxybenzyl 4-bromo-6,6,6-trichlorohexanoate was treated with 7.4 g of piperidine. Chromatography of the crude reaction product on a charcoal column using benzene as the eluent gave 13.5 g of 3-phenoxybenzyl 3,3-dimethyl-6,6,6-trichloro-4-hexenoate.

NMR spectrum (δ ppm): 7.4–6.7 (m, 9H), 6.23 (d, 1H), 5.95 (d, 1H), 4.93 (s, 2H), 2.33 (s, 2H), 1.18 (s, 6H).

IR spectrum (peaks, cm$^{-1}$): 1740, 1650, 1590, 1490, 1450, 1260, 1220, 1160, 1120, 1080, 965, 940, 850, 730, 695.

Elemental analysis: Calc. for $C_{21}H_{21}O_3Cl_3$: C, 59.0; H, 5.0; Cl, 24.9. Found: C, 58.5; H, 4.8; Cl, 25.3.

We claim:

1. In a process for preparing a 6,6,6-trihalo-3,3-dimethyl-4-hexenoate by dehydrohalogenating a 4,6,6,6-tetrahalo-3,3-dimethylhexanoate, the improvement which comprises dehydrohalogenating with an organic amine a 4,6,6,6-tetrahalo-3,3-dimethylhexanoate having a 4-halogen atom of higher atomic number than any of the 6-halogen atoms, producing the 6,6,6-trihalo-3,3-dimethyl-4-hexenoate.

2. The process of claim 1 wherein the organic amine is piperidine.

3. The process of claim 2 wherein the 4-halogen atom in the 4,6,6,6-tetrahalo-3,3-dimethylhexanoate is bromine.

4. The process of claim 3 wherein the 4,6,6,6-tetrahalo-3,3-dimethylhexanoate and the 6,6,6-trihalo-3,3-dimethyl-4-hexenoate are lower alkyl esters.

5. The process of claim 4 wherein methyl 6,6,6-trichloro-3,3-dimethyl-4-hexenoate is prepared from methyl 4-bromo-6,6,6-trichloro-3,3-dimethylhexanoate.

6. The process of claim 4 wherein ethyl 6,6,6-trichoro-3,3-dimethyl-4-hexenoate is prepared from ethyl 4-bromo-6,6,6-trichloro-3,3-dimethylhexanoate.

7. The process of claim 3 wherein the 4,6,6,6-tetrahalo-3,3-dimethylhexanoate and the 6,6,6-trihalo-3,3-dimethyl-4-hexeneoate are 3-phenoxybenzyl, α-cyano-3-phenoxybenzyl, or 5-benzyl-3-furylmethyl esters.

8. The process of claim 7 wherein 3-phenoxybenzyl 6,6,6-trichloro-3,3-dimethyl-4-hexenoate is prepared from 3-phenoxybenzyl 4-bromo-6,6,6-trichloro-3,3-dimethylhexanoate.

9. Methyl 3,3-dimethyl-6,6,6-trichloro-4-hexenoate.

10. 3-Phenoxybenzyl 3,3-dimethyl-6,6,6-trichloro-4-hexenoate.

* * * * *